US012111197B2

(12) United States Patent
Bruder et al.

(10) Patent No.: US 12,111,197 B2
(45) Date of Patent: *Oct. 8, 2024

(54) QUALITY CONTROL SYSTEM FOR ANALYZING THE QUALITY OF A BATTERY CELL THROUGH A VOLUMETRIC MEASUREMENT OF GAS FORMED DURING A CELL FORMATION PROCESS AND A METHOD OF ANALYZING THE SAME

(71) Applicant: GM Global Technology Operations LLC, Detroit, MI (US)

(72) Inventors: Dmitriy Bruder, Clinton Township, MI (US); James R. Salvador, East Lansing, MI (US); Raffaello Ardanese, Bloomfield Hills, MI (US); Ryan C. Sekol, Grosse Pointe Woods, MI (US); Thomas A. Yersak, Royal Oak, MI (US); Sean Robert Wagner, Shelby Township, MI (US); Ronald M Lesperance, Troy, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 610 days.

This patent is subject to a terminal disclaimer.

(21) Appl. No.: 17/350,644

(22) Filed: Jun. 17, 2021

(65) Prior Publication Data
US 2022/0404186 A1    Dec. 22, 2022

(51) Int. Cl.
*G01F 22/00* (2006.01)
*G01B 3/38* (2006.01)
(Continued)

(52) U.S. Cl.
CPC .............. *G01F 22/00* (2013.01); *G01B 3/38* (2013.01); *G01B 5/06* (2013.01); *G01B 7/18* (2013.01);
(Continued)

(58) Field of Classification Search
CPC .......... G01F 22/00; G01F 23/00; G01B 3/38; G01B 5/06; G01B 7/18; G01B 11/02;
(Continued)

(56) References Cited

U.S. PATENT DOCUMENTS 10,014,561 B2    7/2018    Sood et al.
2013/0260192 A1*  10/2013    LePort ................. H01M 10/42
                                                         429/62
(Continued)

FOREIGN PATENT DOCUMENTS

CN    103344920 B  *  5/2016
CN    211528633 U  *  9/2020
(Continued)

*Primary Examiner* — Marrit Eyassu
(74) *Attorney, Agent, or Firm* — Vivacqua Crane, PLLC

(57) ABSTRACT

A quality control system analyzes the quality of a battery cell, with the battery cell defining a gas pouch configured to expand from a deflated configuration to an inflated configuration when filled with a gas formed during a cell formation process. The system comprises a computational system comprising a processor and a memory and a measurement instrument in electronic communication with the computational system. The measurement instrument is arranged to measure a distance defined by the gas pouch and transmit a signal to the computational system corresponding to the distance. The computational system is arranged to analyze the distance with the processor and determine a volumetric measurement of the gas within the gas pouch and compare the volumetric measurement to a threshold in the memory to assess a quality score for the battery cell. A corresponding method analyzes the quality of the battery cell with the quality control system.

10 Claims, 8 Drawing Sheets

(51) Int. Cl.
  *G01B 5/06* (2006.01)
  *G01B 7/16* (2006.01)
  *G01B 11/02* (2006.01)
  *G01F 23/00* (2022.01)
  *G01N 30/02* (2006.01)
  *G01N 33/00* (2006.01)
  *G06K 7/10* (2006.01)
  *G06T 7/62* (2017.01)
  *H01M 4/02* (2006.01)
  *H01M 4/04* (2006.01)
  *H01M 4/139* (2010.01)
  *H01M 4/62* (2006.01)
  *H01M 10/058* (2010.01)
  *H01M 10/42* (2006.01)
  *H01M 50/609* (2021.01)
  *H01M 10/0525* (2010.01)

(52) U.S. Cl.
  CPC .............. *G01B 11/02* (2013.01); *G01F 23/00* (2013.01); *G01N 30/02* (2013.01); *G01N 33/0027* (2013.01); *G06K 7/10366* (2013.01); *G06T 7/62* (2017.01); *H01M 4/045* (2013.01); *H01M 4/139* (2013.01); *H01M 4/628* (2013.01); *H01M 10/058* (2013.01); *H01M 10/4285* (2013.01); *H01M 50/609* (2021.01); *G01N 2030/025* (2013.01); *H01M 2004/027* (2013.01); *H01M 10/0525* (2013.01)

(58) Field of Classification Search
  CPC ...... G01B 3/56; G01N 30/02; G01N 33/0027; G01N 2030/025; G06K 7/10366; G06K 19/0716; G06K 19/0723; G06T 7/62; G06T 2207/30108; G06T 7/0004; H01M 4/045; H01M 4/139; H01M 4/628; H01M 10/058; H01M 10/4285; H01M 50/609; H01M 10/0525; H01M 2004/027; H01M 10/425; H01M 10/446; H01M 50/105; H01M 2010/4278; H01M 2220/20; Y02E 60/10; G01R 31/36
  USPC ....................................................... 73/23.35
  See application file for complete search history.

(56) References Cited

U.S. PATENT DOCUMENTS

| | | |
|---|---|---|
| 2014/0089692 A1 | 3/2014 | Hanafusa |
| 2014/0266060 A1 | 9/2014 | Mng |
| 2015/0303723 A1 | 10/2015 | Raghavan et al. |
| 2017/0069889 A1 | 3/2017 | Yang |
| 2018/0040926 A1 | 2/2018 | Keser et al. |
| 2020/0292622 A1 | 9/2020 | Wu et al. |
| 2020/0358147 A1* | 11/2020 | Dou .................... G01N 29/262 |
| 2022/0102806 A1 | 3/2022 | Min |
| 2022/0123559 A1* | 4/2022 | Stefanopoulou ......... G09B 5/02 |
| 2022/0399592 A1 | 12/2022 | Schreiber et al. |
| 2022/0404186 A1 | 12/2022 | Bruder |
| 2022/0404325 A1* | 12/2022 | Ardanese ........... G01N 33/0062 |
| 2022/0404431 A1* | 12/2022 | Salvador ................ G01N 30/88 |
| 2023/0040106 A1 | 2/2023 | Youn et al. |
| 2023/0244200 A1* | 8/2023 | Charles ............... H01M 10/441 |
| | | 700/295 |

FOREIGN PATENT DOCUMENTS

| | | | |
|---|---|---|---|
| JP | 2012129023 A | * | 7/2012 |
| JP | 2014127341 A | * | 7/2014 |
| KR | 20220147253 A | | 11/2022 |
| WO | 2020110328 A1 | | 6/2020 |

* cited by examiner

QUALITY CONTROL SYSTEM FOR ANALYZING THE QUALITY OF A BATTERY CELL THROUGH A VOLUMETRIC MEASUREMENT OF GAS FORMED DURING A CELL FORMATION PROCESS AND A METHOD OF ANALYZING THE SAME

INTRODUCTION

The present disclosure relates to a quality control system for analyzing the quality of a battery cell, and more particularly to a quality control system for analyzing the quality of a battery cell through a volumetric measurement of gas formed during a cell formation process, and a method of analyzing the same.

In recent years, the use of electric motors to power vehicles has increased exponentially. To power the electric motors, battery packs comprised of numerous battery cells are utilized. Most battery cells can maintain a charge suitable to power the vehicle over a range of several hundred miles. However, occasionally battery cells are produced of low-quality that are unable to hold a sufficient charge. A common reason for a low-quality battery cell is an insufficient Solid Electrolyte Interphase (SEI) deposited on the anode of the battery cell. The SEI is formed by the reduction of electrolyte solvents, additives, and salts.

Current practices to analyze the quality of battery cells includes performing a discharge capacity check (i.e., checking that the cell provides capacity (measured in amp-hours) that is within a determined specification) and performing an inventory hold and open circuit voltage ("OCV") monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic). Other methods of analyzing the quality of battery cells involve analyzing the SEI on the anode. However, the battery cell must be cut open (destroying the battery cell) to analyze the SEI.

Thus, while current quality control systems for analyzing the quality of a battery cell achieve their intended purpose, there is a need for a new and improved quality control system that addresses these issues.

SUMMARY

According to several aspects of the present disclosure, a quality control system analyzes the quality of a battery cell, with the battery cell defining a gas pouch configured to expand from a deflated configuration to an inflated configuration when filled with a gas formed during a cell formation process of the battery cell. The quality control system comprises a computational system comprising a processor and a memory and a measurement instrument in electronic communication with the computational system. The measurement instrument is arranged to measure a distance defined by the gas pouch and transmit a signal to the computational system corresponding to the distance. The computational system is arranged to analyze the distance with the processor and determine a volumetric measurement of the gas within the gas pouch and compare the volumetric measurement to a threshold in the memory to assess a quality score for the battery cell.

In one aspect, the measurement instrument comprises a caliper having a pair of opposing jaws movable towards and away from one another, with the jaws arranged on opposing sides of the gas pouch to measure the distance.

In another aspect, the jaws are pivotally coupled and further comprise a sensor and wherein the distance is further defined as an angle between the jaws and with the computational system receiving the angle in the signal from the sensor.

In another aspect, the measurement instrument comprises a strain gauge arranged to be applied to the gas pouch in the deflated configuration, with the strain gauge arranged to be placed in tension with the expansion of the gas pouch to the inflated configuration and measure the distance through the tension of the strain gauge.

In another aspect, the measurement instrument comprises a carbon coating deposited on the gas pouch in the deflated configuration, with the resistance of the carbon coating arranged to change with the expansion of the gas pouch to the inflated configuration and measure the distance through the change in the resistance of the carbon coating.

In another aspect, the measurement instrument comprises a sensor electrically coupled to the carbon coating, with the sensor arranged to detect the change in resistance with the expansion of the gas pouch.

In another aspect, the measurement instrument comprises a passive RFID tag disposed on the gas pouch and an RFID reader in wireless communication with the passive RFID tag, with the RFID tag configured to deflect with the gas pouch as the gas pouch fills with gas and expands from the deflated configuration to the inflated configuration, with the deflection of the passive RFID tag configured to change the operable radio frequency between the passive RFID tag and the RFID reader, and with the computational system configured to analyze the change in operable radio frequency and determining the volume of the gas.

In another aspect, the measurement instrument comprises a vision system spaced from the battery cell and arranged to collect at least one image of the battery cell showing the distance and transmit the image to the computational system, with the computational system arranged to analyze the distance in the image and determine the volumetric measurement of the gas within the gas pouch.

In another aspect, the battery cell comprises multiple battery cells, with the vision system arranged to collect the at least one image of the plurality of battery cells.

In another aspect, the measurement instrument comprises an optical distance sensor spaced from the battery cell and arranged to emit light toward the battery cell and receive reflected light from the battery to determine the distance, with the optical distance sensor arranged to transmit the distance to the computational system, and with the computational system arranged to analyze the distance and determine the volumetric measurement of the gas within the gas pouch.

In another aspect, the measurement instrument comprises a vessel defining a chamber having a liquid disposed therein and a sensor in electronic communication with the computational system and arranged to determine the level of the liquid in the chamber, with the gas pouch arranged to be submerged in the liquid, and with expansion of the gas pouch from the deflated configuration to the inflated configuration displacing the liquid and raising level of the liquid the distance, with the sensor arranged to detect and transmit the distance to the computational system.

According to several aspects of the present disclosure, a method of analyzing the quality of a battery cell with a quality control system is disclosed. The quality control system comprises a computational system comprising a processor and a memory and a measurement instrument in electronic communication with the computational system. The method comprises performing a cell formation process of the battery cell, collecting a gas formed during the cell formation process in a gas pouch of the battery cell, and expanding the gas pouch with the gas from a deflated configuration to an inflated configuration. The method further comprises measuring a distance defined by the gas pouch with the measurement instrument, transmitting a signal from the measurement instrument to the computational system corresponding to the distance, and analyzing the distance with the processor of the computational system. The method further comprises determining a volumetric measurement of the gas within the gas pouch with the computational system from the distance, comparing the volumetric measurement with the processor to a threshold in the memory, and assessing a quality score for the battery cell with the computational system based upon the comparison of the volumetric measurement to the threshold.

In one aspect, the method further includes measuring the gas pouch in the deflated configuration with the measurement instrument to establish a baseline and further defines measuring the distance defined on the gas pouch with the measurement instrument as measuring the distance defined by the gas pouch from the baseline with the measurement instrument.

In another aspect, performing the cell formation process of the battery cell is further defined as introducing an electrolyte to an anode within the battery cell and depositing of a solid electrolyte interphase on the anode through an oxidation-reduction reaction with the electrolyte.

In another aspect, the threshold is defined as two thresholds, with one of the threshold about 0.5 mL/Ah and the other one of the thresholds about 3 mL/Ah.

In another aspect, the quality score is a low-quality score for volumetric measurement below 0.5 mL or above 3 mL/Ah.

In another aspect, the method further comprises removing the battery cell from production based upon the quality score and performing additional quality review of the battery cell.

In another aspect, performing additional quality review of the battery cell is further defined as performing gas chromatography on the gas within the gas pouch.

In another aspect, measuring the distance defined by the gas pouch with the measurement instrument is further defined as measuring the distance defined by the gas pouch with the measurement instrument comprising one of a caliper, a strain gauge, a carbon coating, a vision system, and an optical distance sensor.

According to several aspects of the present disclosure, a method of analyzing the quality of a battery cell with a quality control system is disclosed. The quality control system comprises a computational system comprising a processor and a memory and a measurement instrument in electronic communication with the computational system. The method comprises measuring a gas pouch of the battery cell in the deflated configuration with the measurement instrument to establish a baseline, performing a cell formation process of the battery cell, and collecting a gas formed during the cell formation process in the gas pouch. The method further comprises expanding the gas pouch with the gas from a deflated configuration to an inflated configuration, measuring a distance defined by the gas pouch from the baseline with the measurement instrument, and transmitting a signal from the measurement instrument to the computational system corresponding to the distance. The method further comprises analyzing the distance with the processor of the computational system, determining a volumetric measurement of the gas within the gas pouch with the computational system from the distance, and comparing the volumetric measurement with the processor to two thresholds in the memory, with one of the thresholds about 0.5 mL/Ah and the other one of the thresholds about 3 mL/Ah. The method further comprises assessing a quality score for the battery cell with the computational system based upon the comparison of the volumetric measurement to the thresholds, wherein the quality score is a low-quality score for volumetric measurement below 0.5 mL/Ah or above 3 mL/Ah.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
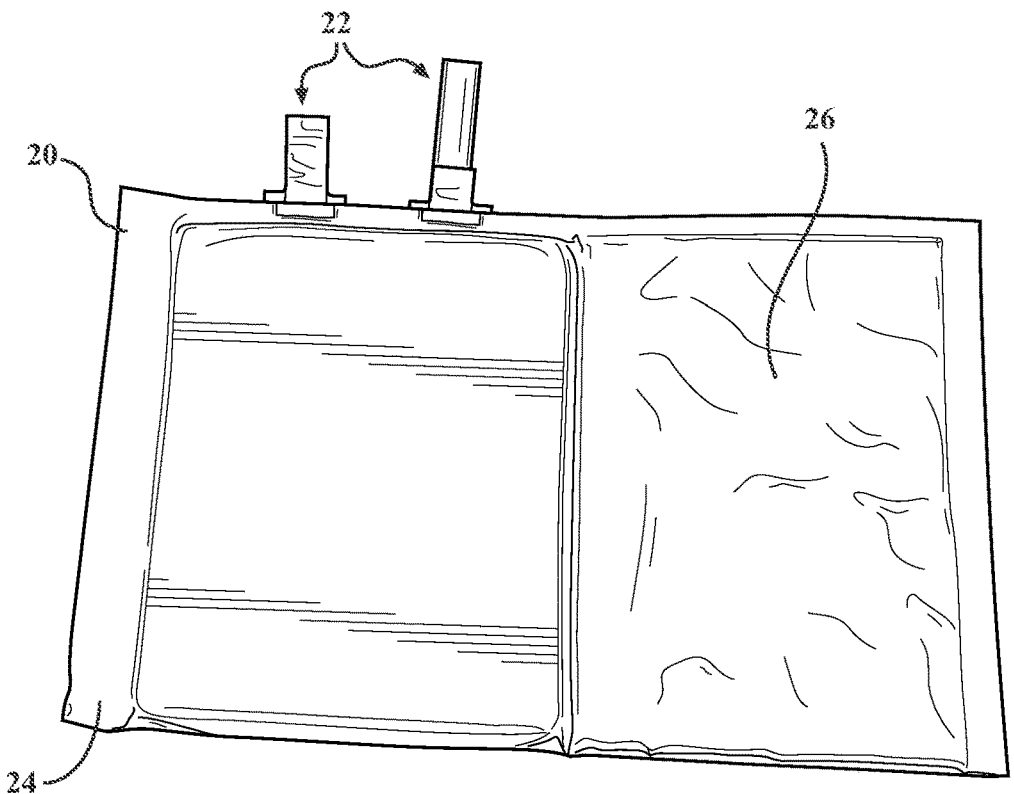
FIG. 1 is a perspective view of one example of a battery cell comprising a gas pouch, with the gas pouch in a deflated configuration.
Figure 2:
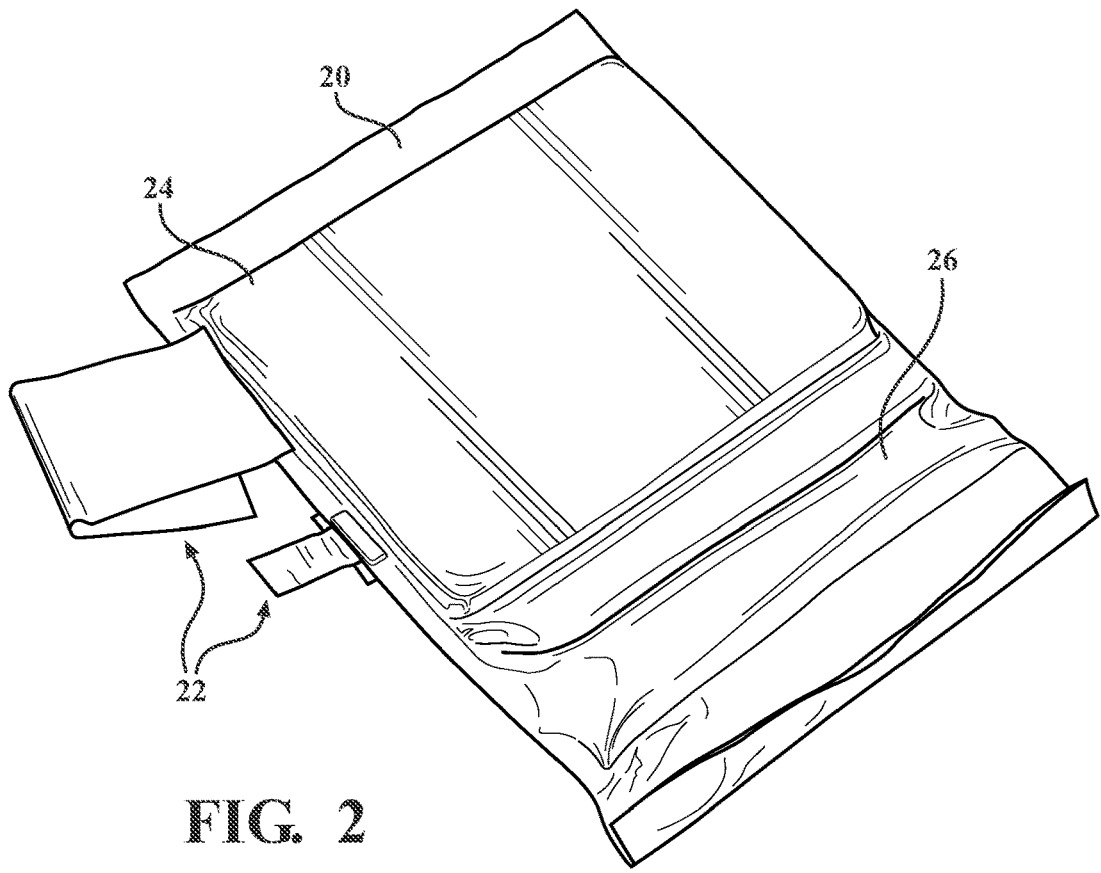
FIG. 2 is a perspective view of the battery cell shown in FIG. 1, with the gas pouch in an inflated configuration.

Referring to FIGS. 1 and 2, according to several aspects of the present disclosure, a battery cell is shown generally at 20. The battery cell 20 is a component of a battery pack. More specifically, the battery pack comprises multiple battery cells 20 that are electrically connected. The common application for such battery cells 20 is in an electric automotive vehicle. However, the battery cells 20 may be utilized in many other applications, such as non-automotive vehicular applications, consumer electronics, etc. The battery cell 20 disclosed herein is a lithium-ion battery cell. The battery cell comprises an electrolyte (not shown) and a pair of electrodes 22 that include an anode and a cathode. The cathode may NCM, NCMA, LMO, LFP, combinations thereof or any like material. The anode may comprise graphite, SiOx, Si, combinations thereof or any like material. The electrolyte may be carbonate based with a fluorinated Li salt. However, battery cells of different chemistries may be utilized.

The battery cell 20 disclosed herein may undergo numerous steps to produce the active battery cell 20. Although steps may vary between different types of battery cells, the battery cell 20 shown herein is produced by first preparing an electrode slurry (not shown) of active material, binder, and conductive agents that are mixed in specific mass ratios. Next, the electrode slurry is coated on collectors and dried. During a calendering process, the porous electrodes 22 are compressed by driving the electrodes 22 through rollers (not shown). The electrodes 22 are then cut or punched into strips that are wound or stacked together with a separator (not shown). The electrodes 22 (comprising an anode and a cathode) are then placed in a sleeve 24 (more specifically, within a cavity defined by the sleeve 24). During a cell formation process, an electrolyte is injected into the cavity. The electrolyte permeates and fills pores within the electrodes 22. A charge is then applied to the electrodes 22 by first applying a constant current to a predetermined first voltage limit, then applying a second constant current to a second voltage limit, and then holding the voltage at the second voltage limit for a predetermined length of time. When the current is applied, the voltage is left to drift according to the charge states of the anode and the cathode.

During the cell formation process, a Solid Electrolyte Interphase (SEI) is deposited on the anode. The SEI (not shown) is formed by the reduction of electrolyte solvents, additives, and salts. The reduction of electrolyte occurs at characteristic voltages and is accompanied by production of gasses which must be vented from the cavity. To this end, the battery cell 20, as shown in FIGS. 1 and 2, further comprises a gas pouch 26 in fluid communication with the cavity. The gas pouch 26 is configured to expand from a deflated configuration to an inflated configuration when filled with the gas formed during the cell formation process of the battery cell 20.

Current practices to analyze the quality of battery cells involves performing a discharge capacity check (i.e., checking that the cell provides capacity (measured in amp-hours) that is within a determined specification) or performing an inventory hold and open circuit voltage ("OCV") monitoring (which involves holding the inventory and checking for a decrease in OCV over time). While effective, such quality control measures are time intensive (with the potential for large quality spills and the added cost of overhead to store inventory) and data poor (i.e., not diagnostic or prognostic).

However, the gas produced by the cell formation process provides data that be used to assess the quality of the battery cell 20. The excessive production of gas can be indicative of a low-quality battery cell 20. More specifically, in one example the battery cell 20 is expected to produce between 0.5 and 3 mL/Ah. If the amount of gas produced is greater than 1.5 mL/Ah, the battery cell 20 may be low-quality. The excessive gas may be due to several reasons. As one example, the complete inactivity of electrolyte additives such as vinyl carbonate ("VC"), vinyl ethylene carbonate ("VEC"), etc. will lead to excessive consumption of ethylene carbonate ("EC") resulting in gas production. In this situation, these battery cells 20 show very poor charge retention with cycling. Poor additive performance due to partial expiration and degradation will also lead to excessive EC consumption and increased gas generation volume though not to the extent as seen in the previous example.

In general, small gas volume results in the highest initial charge capacity of the battery cell 20, while an increase in gas volume (due to EC reduction) is correlated to degradation of charge capacity over time. Excessive Ethylene Carbonate (EC) reduction during the formation cycle consumes lithium salt in the electrolyte, which lowers the total available "lithium inventory" in the battery cell 20, which reduces ultimate charge capacity. Poor electrolyte additive performance causes a more rapid breakdown of the SEI layer. As a result, additional EC reduction is necessary to maintain the SEI layer. The SEI layer formed primarily from EC reduction has poor mechanical properties and greater thickness, which is inferior to one formed when electrolyte additives are present.

To this end, a quality control system 28 for analyzing the quality of the battery cell 20 is disclosed herein and shown in FIGS. 3A-9B. The quality control system 28 comprises a computational system 30 comprising a processor 31 and a memory 33 comprising program instructions. The memory 33 may be further defined as a non-transitory computer-readable medium which includes, but is not limited to, random access memory (RAM), hard disk drive, and a flash drive. The quality control system 28 further comprises a measurement instrument 32 in electronic communication with the computational system 30. The measurement instrument 32 is arranged to measure a distance D defined by the gas pouch 26 and transmit a signal to the computational system 30 corresponding to the distance D. The computational system 30 is arranged to analyze the distance D with the processor 31 and determine a volumetric measurement of the gas within the gas pouch 26 and compare the volumetric measurement to a threshold in the memory 33 to assess a quality score for the battery cell 20.

More specifically, the computational system 30 has access in the memory 33 to measurement attributes of the gas pouch 26 in relation to a range of volumes from the deflated configuration to the completely inflated configuration. Based upon the signal from the measurement instrument 32, the computational system 30 can ascertain the volume within the gas pouch 26. Furthermore, as described above, the gas pouch 26 may have the threshold (or thresholds) for the volume that define a low-quality battery cell 20 (e.g., above 3 mL/Ah). In this context, the term "about" is known to those skilled in the art. Alternatively, the term "about" may be read to mean plus or minus 0.5 mL. Based upon the volume determined by the computational system 30 in comparison with the known thresholds, the computational system 30 will assess the quality score for the battery cell 20. Depending on the quality score, the battery cell 20 may continue through production, may be withdrawn from production for further quality assessment, or may be removed entirely from production (i.e., scrapped).

Figure 3A:
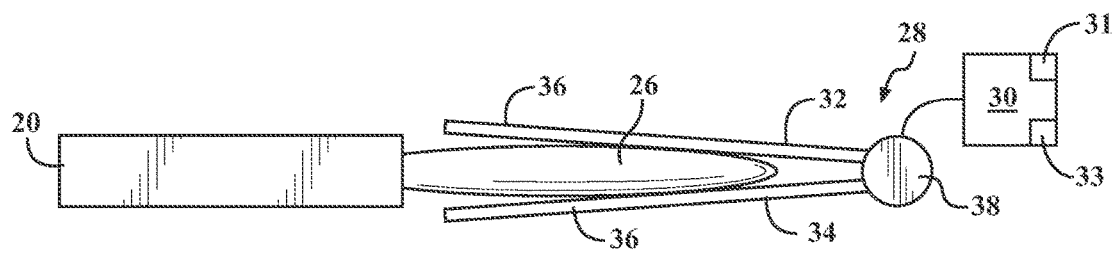
FIG. 3A is a schematic view of one example of a quality control system comprising a caliper and the battery cell of FIG. 1 in the deflated configuration.
Figure 3B:
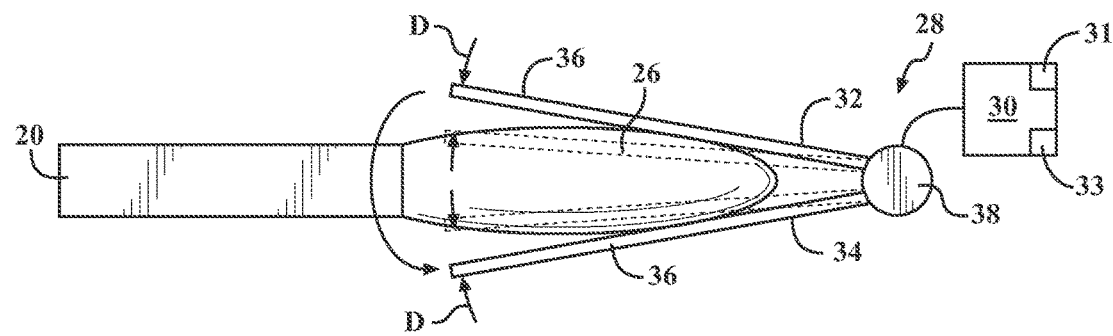
FIG. 3B is a schematic view of the quality control system of FIG. 3A, with the battery cell in the inflated configuration.

In the example shown in FIGS. 3A and 3B, the measurement instrument 32 comprises a caliper 34 having a pair of opposing jaws 36 movable towards and away from one another, with the jaws 36 arranged on opposing sides of the gas pouch 26 to measure the distance D. The gas pouch 26 is measured by the caliper 34 in the deflated configuration (see FIG. 3A) and the inflated configuration (see FIG. 3B), with the distance D being the difference in measurement between the deflated and inflated configurations. As shown in FIGS. 3A and 3B, the jaws 36 are pivotally coupled. A sensor 38 is disposed at the pivot. In other examples, the jaws 36 may move translationally or in any other suitable manner.

In this example the distance D is defined between the jaws 36. More specifically, the distance D is further defined as the angle between the jaws 36 with the computational system 30 receiving the angle in the signal from the sensor 38. In other examples, the distance D may be a linear measurement between the jaws 36, a circumferential measurement along the gas pouch 26, or any other suitable manner of measurement between the jaws 36.

The volume of gas formed in the gas pouch 26 during the cell formation process is proportional to the gas mixture concentration distribution and total pressure (assuming ideal gas and using Amagat's Law of partial volumes). As the volume of gas formed inside the gas pouch 26 increases, the internal pressure will also increase and the gas pouch 26 will expand. The change in angle of the jaws 36 is proportional to the change in volume. The relationship is linear up to the point the gas pouch 26 material begins to stretch.

In this example, the sensor 38 emits the signal based upon resistance. The resistance changes with the angle of the jaws 36. The change in resistance of the sensor 38 is linearly proportional to the change in the angle of the jaws 36. From the change in resistance, the computational system 30 determines the volume of the gas within the gas pouch 26.

Figure 4A:
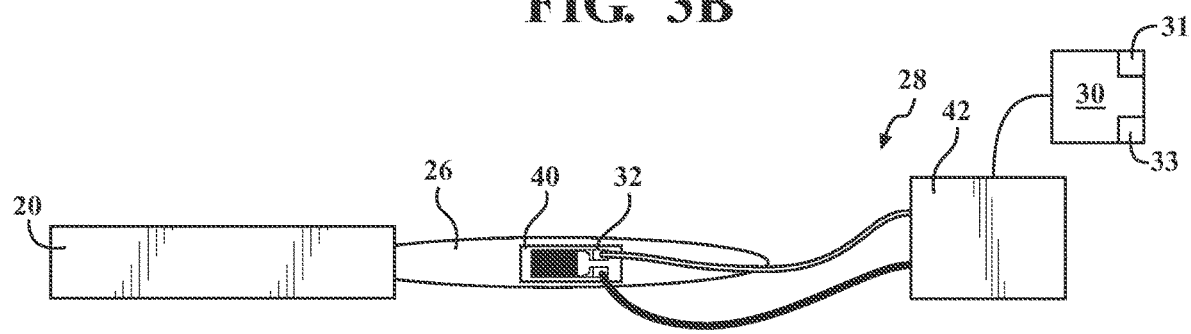
FIG. 4A is a schematic view of another example of the quality control system comprising a strain gauge and the battery cell of FIG. 1 in the deflated configuration.
Figure 4B:
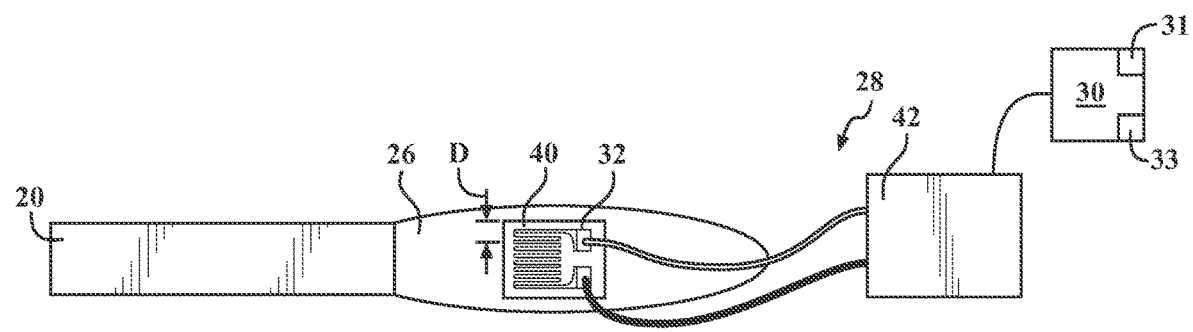
FIG. 4B is a schematic view of the quality control system of FIG. 4A, with the battery cell in the inflated configuration.

In the example shown in FIGS. 4A and 4B, the measurement instrument 32 comprises a strain gauge 40 arranged to be applied to the gas pouch 26 in the deflated configuration, with the strain gauge 40 arranged to be placed in tension with the expansion of the gas pouch 26 to the inflated configuration and measure the distance D through the tension of the strain gauge 40. More specifically, as the gas pouch 26 inflates the strain gauge 40, which is applied to the surface of the gas pouch 26, stretches. The tension that is applied to the strain gauge 40 changes the resistance of the strain gauge 40. A sensor 42, which is electrically coupled to the strain gauge 40, detects the change in resistance from the deflated configuration (see FIG. 4A) to the inflated configuration (see FIG. 4B) and transmits the signal to the computational system 30 with the change in resistance, which the computational system 30 correlates to the distance D (more specifically, the distance D that the strain gauge 40 has stretched). The distance D is correlated to the known volumes for the gas pouch 26 in stored memory 33, from which the computational system 30 ascertains the volume within the gas pouch 26.

In the examples shown in FIGS. 5A-6B, the measurement instrument 32 comprises a carbon coating 44 deposited on the gas pouch 26 in the deflated configuration, with the resistance of the carbon coating 44 arranged to change with the expansion of the gas pouch 26 to the inflated configuration and measure the distance D through the change in the resistance of the carbon coating 44. The carbon coating 44 may be comprised of a polymer, which allows the carbon coating 44 to stretch, and graphite, which is electrically conductive. Therefore, the graphite allows the carbon coating 44 to be electrically coupled to a sensor 46 and the polymer allows the graphite (which is brittle) to flex with the inflation of the gas pouch 26.

As the gas pouch 26 inflates, the carbon coating 44 stretches. The tensile stress that is applied to the carbon coating 44 changes the resistance of the carbon coating 44. The sensor 46 detects the change in resistance from the deflated configuration (see FIGS. 5A and 6A) to the inflated configuration (see FIGS. 5B and 6B) and transmits the signal to the computational system 30 with the change in resistance, which the computational system 30 correlates to the distance D (more specifically, the distance D that the carbon coating 44 has stretched). The distance D is correlated to the known volumes for the gas pouch 26 in stored memory 33, from which the computational system 30 ascertains the volume within the gas pouch 26.

Figure 5A:
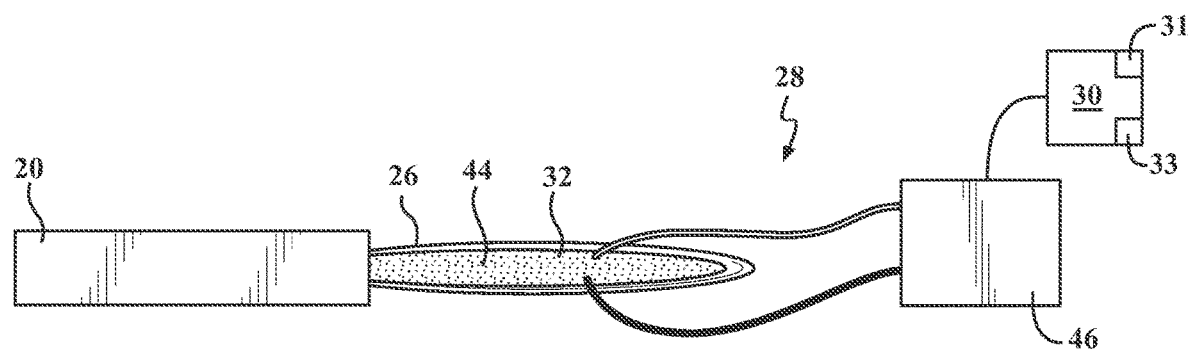
FIG. 5A is a schematic view of another example of the quality control system comprising a carbon coating and the battery cell of FIG. 1 in the deflated configuration.
Figure 5B:
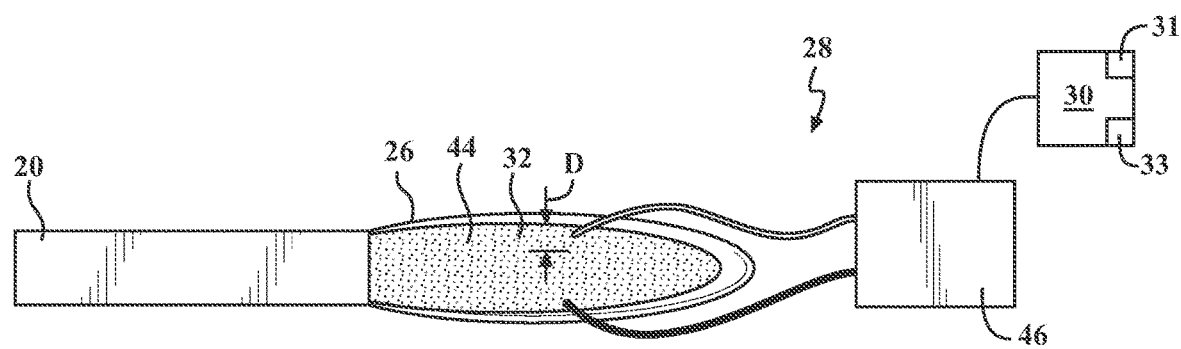
FIG. 5B is a schematic view of the quality control system of FIG. 5A, with the battery cell in the inflated configuration.

In the example shown in FIGS. 5A and 5B, the measurement instrument 32 comprises the sensor 46 electrically coupled to the carbon coating 44, with the sensor 46 arranged to detect the change in resistance with the expansion of the gas pouch 26. More specifically, the sensor 46 is directly wired to the carbon coating 44. In the example shown in FIGS. 6A and 6B, the measurement instrument 32 comprises a passive RFID tag 48 disposed on the gas pouch 26 and electrically coupled to the carbon coating 44 and an RFID reader 50 in wireless communication with the passive RFID tag 48, with the passive RFID tag 48 arranged to wirelessly transmit the change in resistance to the RFID reader 50 to detect the expansion of the gas pouch 26. More specifically, the RFID reader 50 is configured as the sensor 46. The RFID reader 50 transmits the signal to the computational system 30.

Figure 6A:
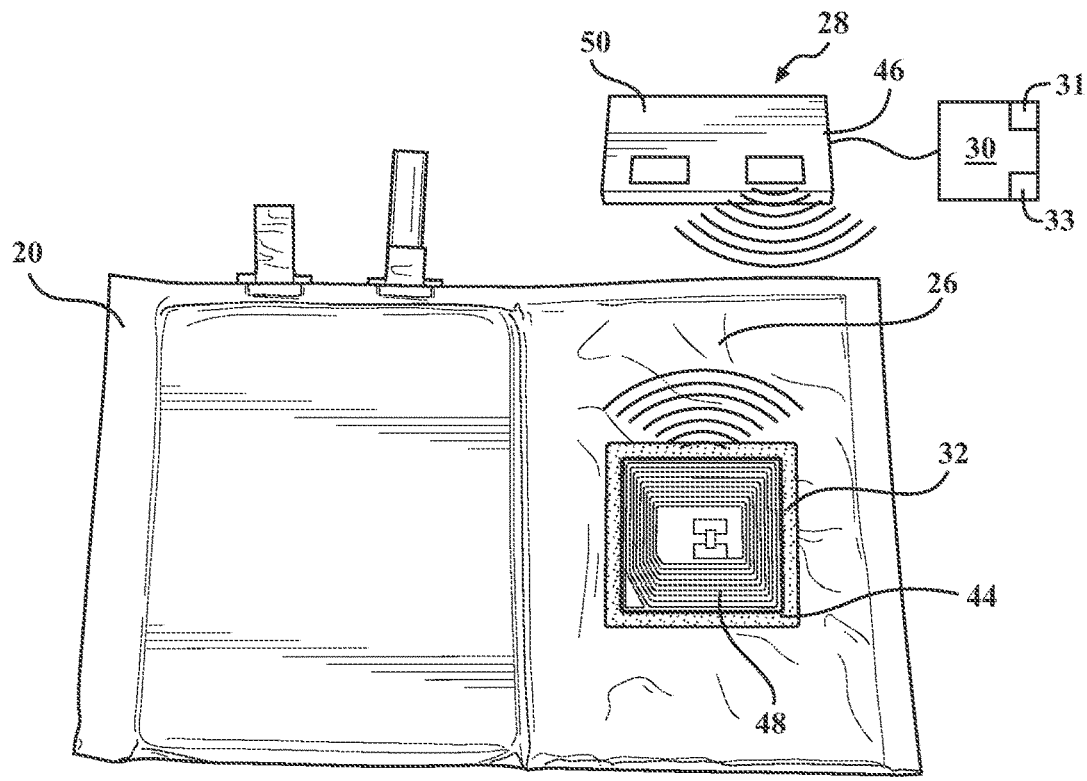
FIG. 6A is a perspective view of another example of the quality control system comprising a passive RFID tag and RFID reader and the battery cell of FIG. 1 in the deflated configuration.
Figure 6B:
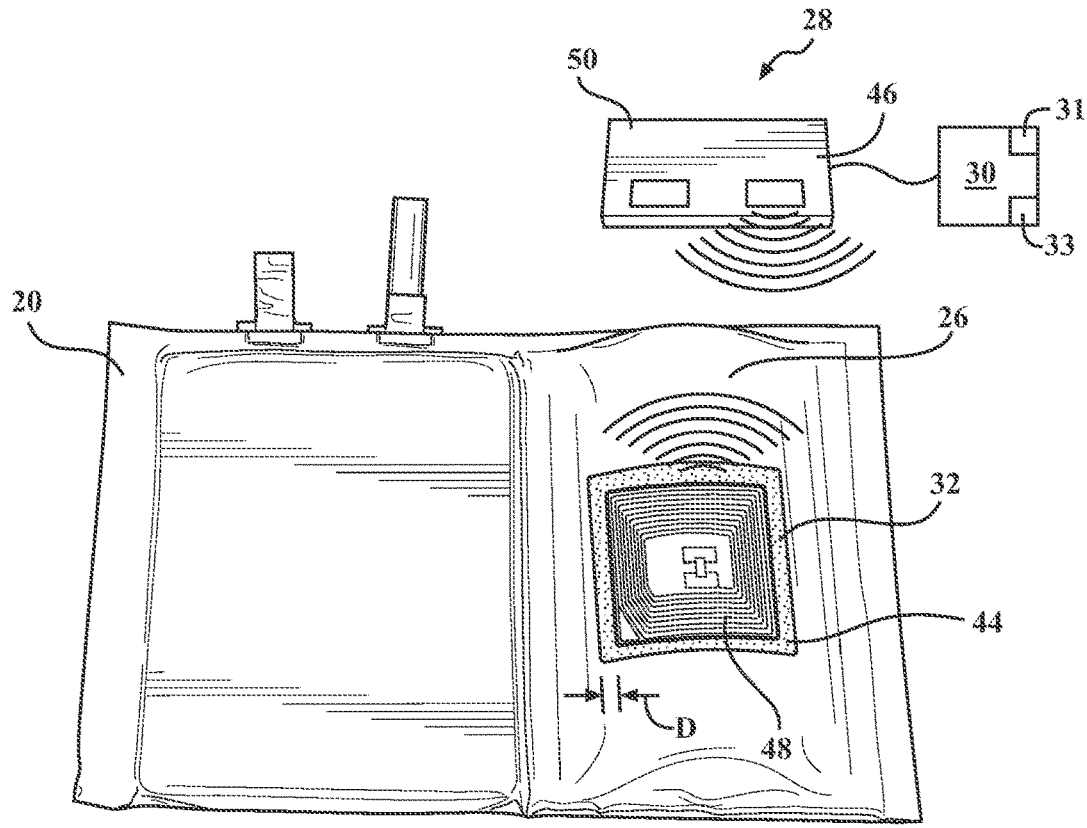
FIG. 6B is a perspective view of the quality control system of FIG. 6A, with the battery cell in the inflated configuration.

Alternatively, the computational system 30 may obtain the distance D directly from fluctuations of the passive RFID tag 48 shown in FIGS. 6A and 6B with the inflation of the gas pouch 26. More specifically, the RFID tag 48 may be disposed on the gas pouch 26 and configured to deflect with the gas pouch 26 as the gas pouch 26 fills with gas and expands from the deflated configuration to the inflated configuration. The deflection of the passive RFID tag 48 changes the operable radio frequency between the passive RFID tag 48 and the RFID reader 50, with the computational system 30 analyzing the change in operable radio frequency and determining the volume of the gas. More specifically, as the gas pouch 26 deforms due to the gas production, the geometry of the RFID tag 48 would change by applying a tension thereon from the gas pouch 26. The capacitor and inductor embedded on the RFID tag 48 will change their nominal values and therefore absorb at a different frequency than when the RFID tag 48 is flat on the gas pouch 26 in the deflated configuration. The RFID tag 48 is queried by a narrow band of RF frequencies and if the wireless signal is not adequately absorbed it indicates that the volume of the gas is out of its specified range. When the wireless signal is out the specified range, the computational system 30 interprets the volume of the gas pouch 26 being greater than the threshold volume.

Figure 7:
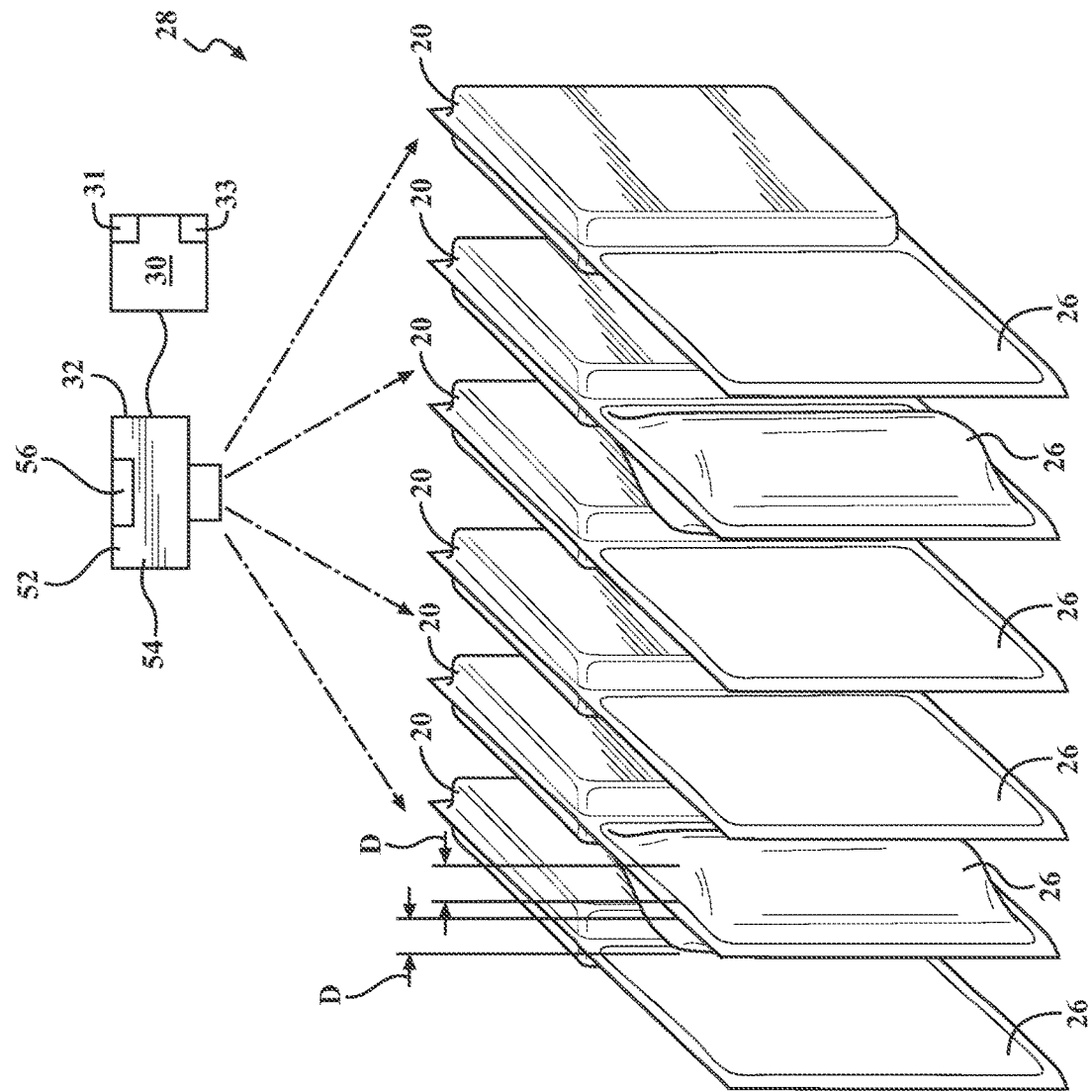
FIG. 7 is a schematic view of another example of the quality control system comprising a vision system and a perspective view of a plurality of the battery cell of FIG. 1 in deflated and inflated configurations.

In the example shown in FIG. 7, the measurement instrument 32 comprises a vision system 52 spaced from the battery cell 20 and arranged to collect at least one image of the battery cell 20 showing the distance D and transmit the image to the computational system 30, with the computational system 30 arranged to analyze the distance D in the image and determine the volumetric measurement of the gas within the gas pouch 26. In the example shown in FIG. 7, the vision system 52 is a camera 54. The camera 54 is configured to take a two-dimension ("2D") image. In this example, the vision system 52 is arranged in a top-down configuration (i.e., the camera 54 is disposed at a longitudinal end of the gas pouch 26 and is imaging the side profile of the gas pouch 26). The camera 54 takes an image of the side profile, which shows the distance D (or plurality of distances) across the gas pouch 26. The camera 54 (which comprises a vision-based sensor 56) sends the image to the computational system 30 through the signal. The computational system 30 then analyzes the image with an image analysis software. The images will provide information through the pixels within the image. The pixel information may directly correspond to a coordinate space. The pixel location information may also correspond to a relative known sensor location in physical coordinate space. Alternatively, the pixel information may include pouch profile change information extracted from side view of pouch during formation, etc. (depending on whether the sensor is a 3D based vision sensor or 2D based sensor). From the relative location of the pixels, the distance D (or plurality of distances) can be derived. The pixel information is then analyzed by the computational system 30 to determine volume. The computational system may compare the distance D to the known volumes for the gas pouch 26 in stored memory 33, from which the computational system 30 ascertains the volume within the gas pouch 26.

Alternatively, the vision system 52 may be configured to take a three-dimensional ("3D") image. The vision system 52 may utilize an array of cameras 54 spaced three-dimensionally about the battery cell 20, with each of the cameras 54 taking images of the gas pouch 26 from different angles. Each of the images shows the distance D (or plurality of distances) across the gas pouch 26. Each camera 54 sends their respective image to the computational system 30 through the signal. The cameras 54 are calibrated to a common 3D coordinate system. The computational system 30 then analyzes the images with an image analysis software (such as a point cloud analytical software) and utilizes the distances D to build a 3D image of the gas pouch 26. From the 3D image the computational system 30 ascertains the volume within the gas pouch 26.

As shown in FIG. 7, the battery cell 20 may be arranged as multiple battery cells 20, with the vision system 52 arranged to collect at least one image of the multiple battery cells 20. However, the vision system 52 may be arranged to collect the image of a single battery cell 20.

Figure 8A:
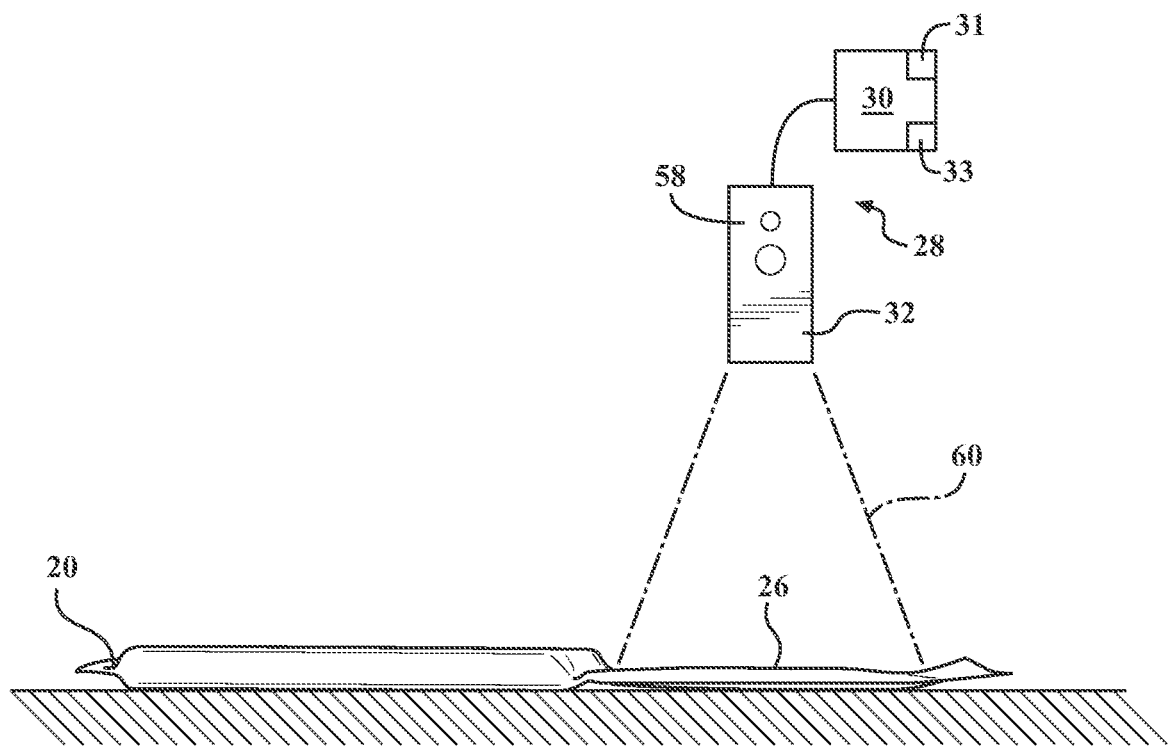
FIG. 8A is a schematic view of another example of the quality control system comprising an optical distance sensor and a side elevational view of the battery cell of FIG. 1 in the deflated configuration.
Figure 8B:
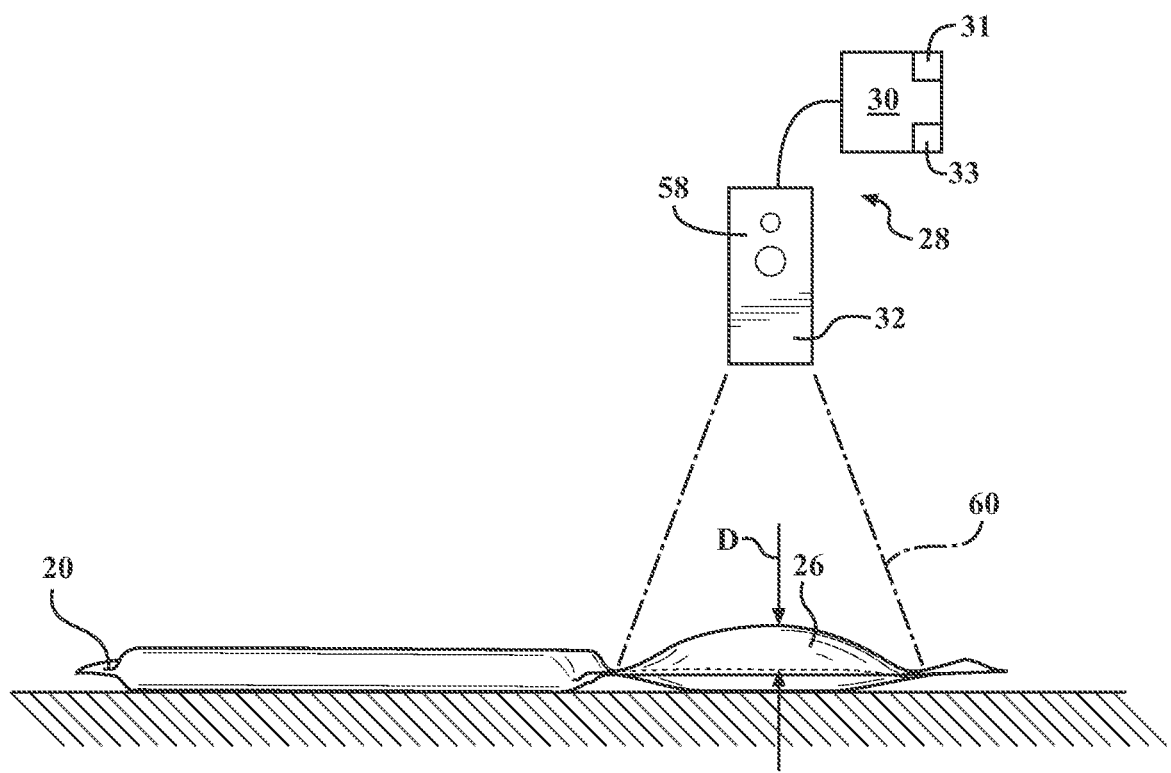
FIG. 8B is a schematic view of the quality control system of FIG. 8A, and a side elevational view of the battery cell in the inflated configuration.

In the example shown in FIGS. 8A and 8B, the measurement instrument 32 comprises an optical distance sensor 58 spaced from the battery cell 20 and arranged to emit light 60 toward the battery cell 20 and receive reflected light 60 from the battery to determine the distance D, with the optical distance sensor 58 arranged to transmit the distance D to the computational system 30, and with the computational system 30 arranged to analyze the distance D and determine the volumetric measurement of the gas within the gas pouch 26. The optical distance sensor 58 is configured to emit the light 60 (e.g., infrared, laser, etc.) toward the gas pouch 26. The gas pouch 26 reflects the light 60 back to the optical distance sensor 58. From variances between the projected and reflected light 60 (such as intensity, angle, time of travel, etc.), the distance D to the gas pouch 26 is determined and sent in the signal to the computational system 30. The distance D from the optical distance sensor 58 may be measured in the both the deflated configuration (see FIG. 8A) and the inflated configuration (see FIG. 8B), with the difference between the two defining the distance D which the gas pouch 26 expands. The distance D is correlated to the known volumes for the gas pouch 26 in stored memory 33, from which the computational system 30 ascertains the volume within the gas pouch 26. Furthermore, a plurality of the optical distance sensor 58 may be utilized to provide several distances D from which a more accurate gas volume may be derived.

Figure 9A:
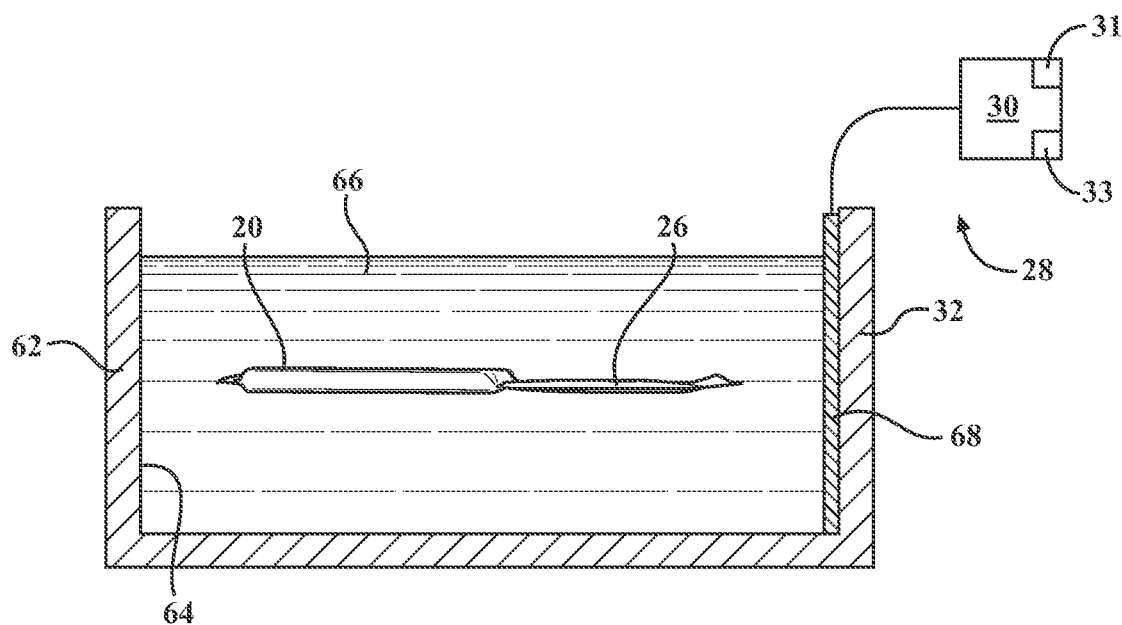
FIG. 9A is a schematic view of another example of the quality control system comprising a vessel and the battery cell of FIG. 1 in the deflated configuration.
Figure 9B:
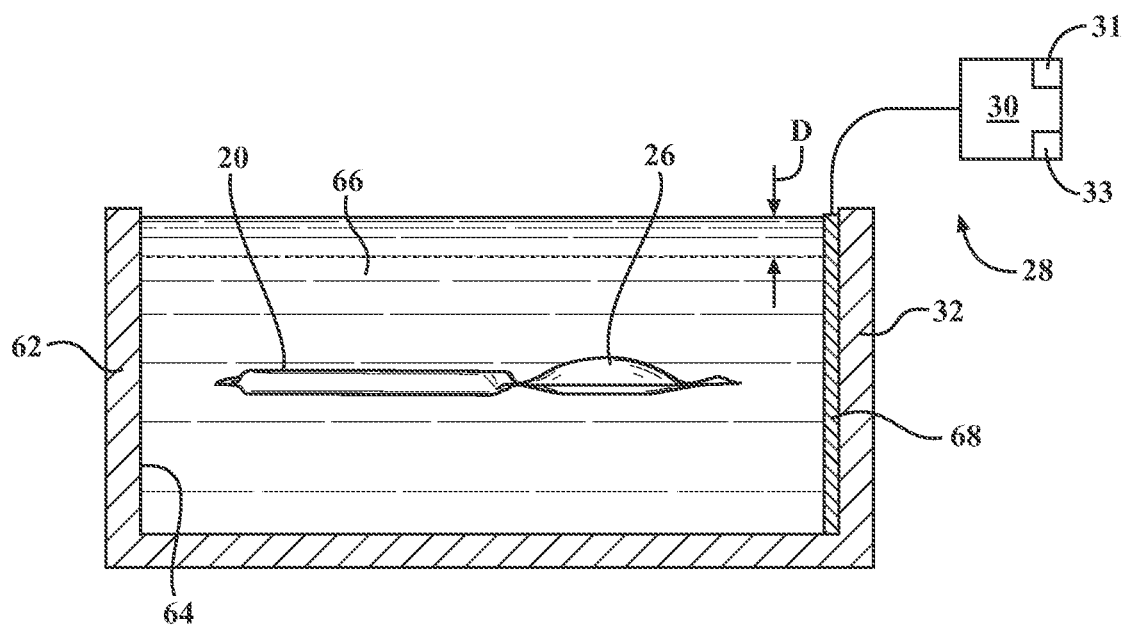
FIG. 9B is a schematic view of the quality control system of FIG. 9A, with the battery cell in the inflated configuration.

In the example shown in FIGS. 9A and 9B, the measurement instrument 32 comprises a vessel 62 defining a chamber 64 having a liquid 66 disposed therein and a sensor 68 in electronic communication with the computational system 30 and arranged to determine the level of the liquid 66 in the chamber 64. The gas pouch 26 is arranged to be submerged in the liquid 66. Expansion of the gas pouch 26 from the deflated configuration (see FIG. 9A) to the inflated configuration (see FIG. 9B) displaces the liquid 66 and raises the level of the liquid 66 the distance D. The sensor 68 is arranged to detect and transmit the distance D to the computational system 30. The computational system 30 then multiplies the distance D to the known cross-sectional area of the vessel 62 to determine the volume of gas within the gas pouch 26. The above-mentioned examples may be performed in-situ (i.e., during the cell formation process) or ex-situ (i.e., after the cell formation process).

Figure 10:
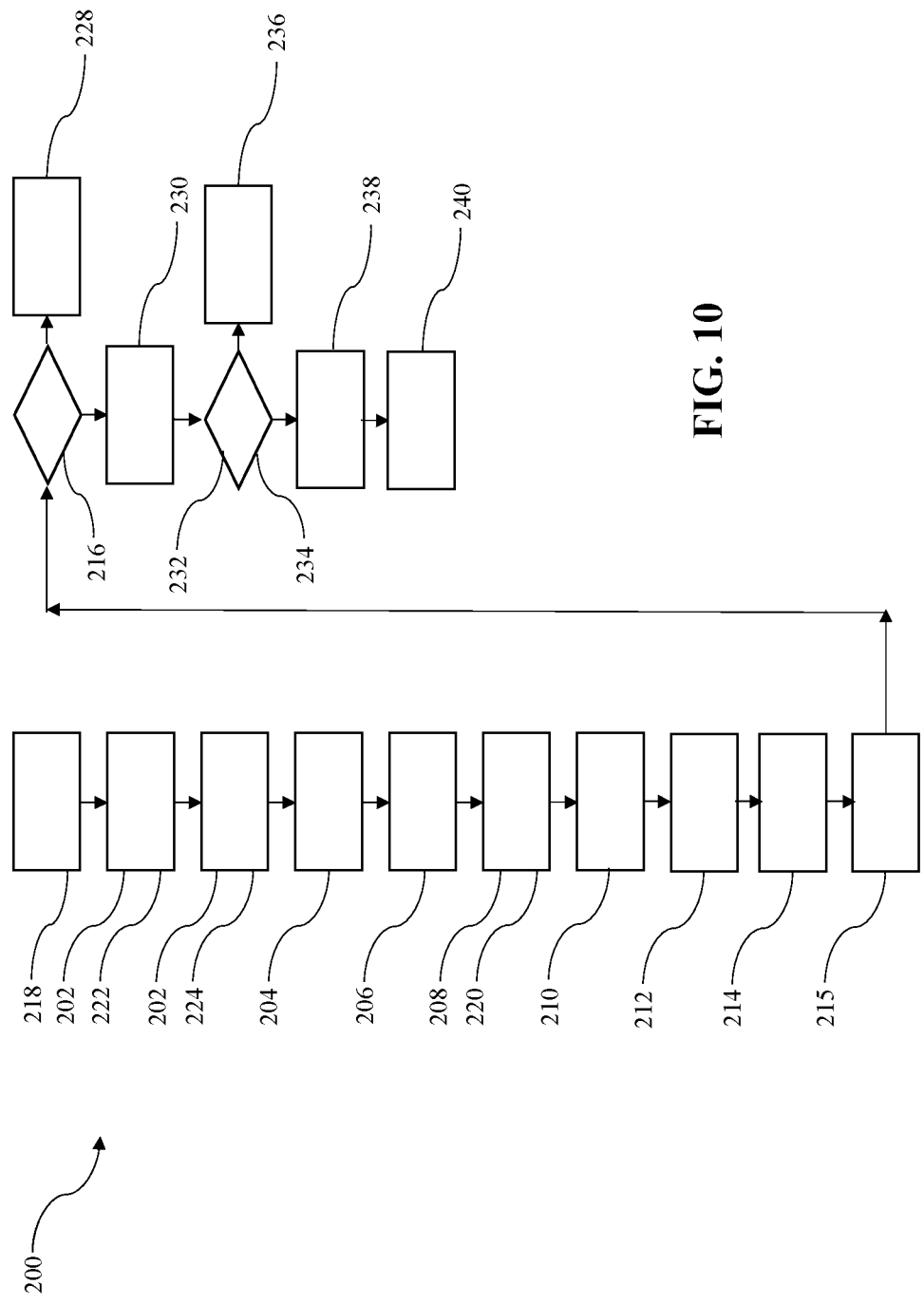
FIG. 10 is a flow chart of one example of a method of analyzing the quality of a battery cell with the quality control system.

A method 200 of analyzing the quality of the battery cell 20 with the quality control system 28 is also disclosed herein and shown in FIG. 10. The method 200 comprises performing the cell formation process of the battery cell 20 as shown in box 202, collecting the gas formed during the cell formation process in the gas pouch 26 of the battery cell 20 as shown in box 204, and expanding the gas pouch 26 with the gas from the deflated configuration to the inflated configuration as shown in box 206. The method 200 further comprises measuring the distance D defined by the gas pouch 26 with the measurement instrument 32 as shown in box 208. Measuring the distance may be further defined as measuring the distance defined by the gas pouch 26 with the measurement instrument 32 comprising one of the caliper 34, the strain gauge 40, the carbon coating 44, the vision system 52, and the optical distance sensor 58. The method 200 further comprises transmitting the signal from the measurement instrument 32 to the computational system 30 corresponding to the distance D as shown in box 210 and analyzing the distance D with the with the processor 31 of the computational system 30 as shown in box 212. The method 200 further comprises determining the volumetric measurement of the gas within the gas pouch 26 with the computational system 30 from the distance D as shown in box 214, comparing the volumetric measurement with the processor 31 to the threshold in the memory 33 as shown in box 215, and assessing the quality score for the battery cell 20 with the computational system 30 as shown in box 216.

The method 200 may further include measuring the gas pouch 26 in the deflated configuration with the measurement instrument 32 to establish a baseline as shown in box 218 and further defines measuring the distance D defined on the gas pouch 26 with the measurement instrument 32 as shown in box 208 as measuring the distance D defined by the gas pouch 26 from the baseline on the gas pouch 26 with the measurement instrument 32 as shown in box 220. More specifically, the method 200 utilizes two measurements (before and after inflation) to define the distance D from which the volume will be measured.

Performing the cell formation process of the battery cell 20 as shown in box 202 may be further defined as introducing an electrolyte to the anode within the battery cell 20 as shown in box 222 and depositing of the solid electrolyte interphase on the anode through an oxidation-reduction reaction with the electrolyte as shown in box 224. The reduction of the electrolyte and the corresponding cell formation process are described in greater detail above.

In the example of the battery cell 20 provided herein, the battery cell 20 is expected to produce between about 0.5-3 ml/Ah of gas. Therefore, the threshold may be defined as two thresholds, with one of the thresholds about 0.5 mL/Ah and the other one of the thresholds about 3 mL/Ah. The quality score may be a low-quality score for the volumetric measurement below 0.5 mL/Ah or above 3 mL/Ah. However, the amount of gas that is expected to be produced during the cell formation process may vary between different battery cells as well as with different additive formulation within the electrolyte.

The method 200 may further comprise continuing production of the battery cell 20 as shown in box 228. The method 200 may further comprise removing the battery cell 20 from production based upon the quality score as shown in box 230. More specifically, if the computational system 30 assesses the quality score and the quality score is indicative of a low-quality battery cell 20, the battery cell 20 may be removed from production. If the battery cell 20 is removed from production, the method 200 may further comprise performing additional quality review of the battery cell 20 as shown box 232. In one example, performing additional quality review of the battery cell 20 is further defined as performing gas chromatography on the gas within the gas pouch 26 as shown in box 234. More specifically, the gas within the gas pouch 26 is removed from the gas pouch 26 and passed through a gas chromatograph. Gas chromatography is the process of separating compounds in gas disposed within the gas pouch 26, allowing for a thorough analysis of the composition of the gas. The composition of the gas in the low-quality battery cell 20 can be compared to a known composition found in healthy battery cell 20. The deviations in the composition may be used to determine the root cause of the low-quality battery cell 20 (e.g., no additives, lean electrolyte, aged electrolyte, humidity, etc.).

The method 200 may further comprise reintroducing the battery cell 20 into production as shown in box 236. More specifically, if after performing the additional quality review, the battery cell 20 is found to have a quality that falls within a desired specification, the battery cell 20 may be placed back into production and sold individually, as part of the battery pack, or in any other configuration. On the other hand, the method 200 may further comprise scrapping the battery cell 20 as shown in box 238 (i.e., permanently removing the battery cell 20 from production). The battery cell 20 may be disassembled and components may be utilized for recycling. Furthermore, the method 200 may further comprise altering the production of the battery cell 20 as shown in box 240. More specifically, if the root cause of the low-quality battery cell 20 may be ascertained, the production of the battery cell 20 may be adjusted to ensure the future production of battery cell 20s that fall within desired quality specifications. In one example, altering the production of the battery cell 20 is further defined as providing instructions for adaptive formation charge parameters. Adaptive formation charge parameters refer to performing corrective action to the cell formation process.

More specifically, data from the cell formation process (such as voltage, current, pressure and temperature versus time) is monitored in real time and (if necessary) corrective actions on the formation schedule could be implemented to ensure desired SEI formation based upon feedback from the comprehensive quality check. Corrective action may include the processor of the computational system (or another computational system within a network) instructing a power supply to apply a corrected constant current or hold a corrected first and/or second voltage limit for a subsequent battery cell 20 during the cell formation process. The computational system may also instruct a temperature control module to correct the ambient temperature of the subsequent battery cell 20 (e.g., with a heater and/or an air conditioner) during the cell formation process. The data from the cell formation process, along with the analysis result from the comprehensive quality check and modified actions to the cell formation process may be archived in a networked repository. Information from this repository could be used to further analyze cell quality down the manufacturing line.

Accordingly, the quality control system 28 and the corresponding method 200 of analyzing the quality of a battery cell 20 with a quality control system 28 offer several advantages. Checking the quality of the battery cell 20 during and/or after the cell formation process reduces the need to perform lengthy inventory holds and open circuit voltage monitoring as currently practiced, which increases manufacturing throughput. Furthermore, analysis of the gas produced by the cell formation process provides data that be used to assess the quality of the battery cell 20 and the oxidation-reduction therein, without destroying a battery cell 20 to analyze the SEI on the anode.

The description of the present disclosure is merely exemplary in nature and variations that do not depart from the general sense of the present disclosure are intended to be within the scope of the present disclosure. Such variations are not to be regarded as a departure from the spirit and scope of the present disclosure.

What is claimed is:

1. A quality control system for analyzing the quality of a battery cell, with the battery cell defining a gas pouch configured to expand from a deflated configuration to an inflated configuration when filled with a gas formed during a cell formation process of the battery cell, the quality control system comprising:
    a computational system comprising a processor and a memory; and
    a measurement instrument in electronic communication with the computational system, wherein the measurement instrument is a vision system disposed apart from the battery cell and imaging a side profile of the gas pouch, wherein the vision system is configured to collect an image of the side profile of the gas pouch, wherein the image includes a distance D defined as a width of the side profile of the gas pouch, and wherein the measurement system is configured to transmit the image to the computational system;
    wherein the computational system is arranged to analyze the image with the processor and determine a volumetric measurement of the gas within the gas pouch by first determining the distance D from the image using pixel information, and then using the distance D and a known cross-sectional area of the gas pouch to determine the volumetric measurement, and wherein the computational system is arranged to compare the volumetric measurement to a first threshold and to a second threshold each stored in the memory to assess a quality score for the battery cell, wherein the first threshold is less than the second threshold, and wherein the quality score is a low-quality score when the volumetric measurement is below the first threshold and the quality score is a low-quality score when the volumetric measurement is above the second threshold.

2. The quality control system of claim 1, wherein the battery cell comprises multiple battery cells, with the vision system arranged to collect the at least one image of the plurality of battery cells.

3. A method of analyzing the quality of a battery cell with a quality control system comprising a computational system comprising a processor and a memory and a measurement instrument in electronic communication with the computational system, the method comprising:
  performing a cell formation process of the battery cell;
  collecting a gas formed during the cell formation process in a gas pouch of the battery cell;
  expanding the gas pouch with the gas from a deflated configuration to an inflated configuration;
  measuring a distance D defined by the gas pouch with the measurement instrument, wherein the measurement instrument is a vision system disposed apart from the battery cell and imaging a side profile of the gas pouch, wherein the vision system is configured to collect an image of the side profile of the gas pouch, wherein the image includes the distance D defined as a width of the side profile of the gas pouch;
  transmitting the image from the measurement instrument to the computational system corresponding to the distance;
  analyzing the image with the processor of the computational system by first determining the distance D from the image using pixel information;
  determining a volumetric measurement of the gas within the gas pouch with the computational system from the distance D and a known cross-sectional area of the gas pouch to determine the volumetric measurement;
  comparing the volumetric measurement with the processor to a first threshold and a second threshold stored in the memory, wherein the first threshold is less than the second threshold; and
  assessing a quality score for the battery cell with the computational system based upon the comparison of the volumetric measurement to the threshold, wherein the quality score is a low-quality score when the volumetric measurement is below the first threshold and the quality score is a low-quality score when the volumetric measurement is above the second threshold.

4. The method as set forth in claim 3, further including measuring the gas pouch in the deflated configuration with the measurement instrument to establish a baseline and further defining measuring the distance defined on the gas pouch with the measurement instrument as measuring the distance defined by the gas pouch from the baseline with the measurement instrument.

5. The method as set forth in claim 3, wherein performing the cell formation process of the battery cell is further defined as introducing an electrolyte to an anode within the battery cell and depositing of a solid electrolyte interphase on the anode through an oxidation-reduction reaction with the electrolyte.

6. The method as set forth in claim 3, wherein the first threshold is about 0.5 mL/Ah and the second threshold is about 3 mL/Ah.

7. The method as set forth in claim 6, the quality score is a low-quality score for volumetric measurement below 0.5 mL or above 3 mL/Ah.

8. The method as set forth in claim 3, further comprising removing the battery cell from production based upon the quality score and performing additional quality review of the battery cell.

9. The method as set forth in claim 8, wherein performing additional quality review of the battery cell is further defined as performing gas chromatography on the gas within the gas pouch.

10. The method of claim 3, further comprising monitoring in real time voltage, current, pressure and temperature versus time of the battery cell and, when the battery cell is assessed a low-quality score, instructing, by the processor, a power supply to apply a corrected constant current or hold a corrected first and/or second voltage limit for a subsequent battery cell during a cell formation process or instructing, by the processor, a temperature control module to correct an ambient temperature of a subsequent battery cell during the cell formation process.

* * * * *